(12) United States Patent
Garcia-Rodenas et al.

(10) Patent No.: US 8,394,370 B2
(45) Date of Patent: *Mar. 12, 2013

(54) NUTRITIONAL FORMULA FOR OPTIMAL GUT BARRIER FUNCTION

(75) Inventors: Clara Lucia Garcia-Rodenas, Forel (CH); Gabriela Bergonzelli, Bussigny-près-Lausanne (CH); Florence Rochat, Montreux (CH); Marco Enrico Turini, Epalinges (CH); Irène Corthesy-Theulaz, Epalinges (CH); Christine Cherbut, Pully (CH)

(73) Assignee: Nestec S.A., Vevey (CH)

( * ) Notice: Subject to any disclaimer, the term of this patent is extended or adjusted under 35 U.S.C. 154(b) by 392 days.

This patent is subject to a terminal disclaimer.

(21) Appl. No.: 10/562,243

(22) PCT Filed: Jun. 22, 2004

(86) PCT No.: PCT/EP2004/006736
§ 371 (c)(1),
(2), (4) Date: Dec. 22, 2005

(87) PCT Pub. No.: WO2004/112509
PCT Pub. Date: Dec. 29, 2004

(65) Prior Publication Data
US 2007/0104700 A1    May 10, 2007

(30) Foreign Application Priority Data

Jun. 23, 2003 (EP) .................................. 03014040

(51) Int. Cl.
*A61K 39/02* (2006.01)
(52) U.S. Cl. .................................................. 424/93.45
(58) Field of Classification Search ........................ None
See application file for complete search history.

(56) References Cited

U.S. PATENT DOCUMENTS

| 6,132,710 A | 10/2000 | Panigrahi et al. |
| 2002/0044988 A1 | 4/2002 | Fuchs et al. |
| 2002/0127211 A1 * | 9/2002 | Brassart et al. ............ 424/93.45 |

FOREIGN PATENT DOCUMENTS

| EP | 0 295 009 | 12/1988 |
| EP | 0 527 283 | 2/1993 |
| EP | 904784 A1 * | 3/1999 |
| EP | 1 064 857 | 1/2001 |
| EP | 1 281 325 | 2/2003 |
| JP | 05-030942 | 2/1993 |
| JP | 05-276894 | 10/1993 |
| JP | 2002-332242 | 11/2002 |
| WO | 97/00078 | 1/1997 |
| WO | 99/56758 | 11/1999 |
| WO | 00/35443 | 6/2000 |
| WO | 01/58283 | 8/2001 |
| WO | WO 01/64225 A1 * | 9/2001 |
| WO | WO 0164225 A1 * | 9/2001 |
| WO | WO 03/041512 A1 * | 5/2003 |
| WO | WO 03041512 A1 * | 5/2003 |

OTHER PUBLICATIONS

Motyl et al., Comp. Biochem. Physiol., 111B:427-433, 1995.*
Birch et al. (Am. J. Clin. Nutr., 75:570-580, 2002).*
Majamaa, H., et al., Probiotics: A novel approach in the management of food allergy; Journal of Allergy and Clinical Immunology, Mosby-Yearly Book, Inc., US, vol. 99, No. 2, 1997, pp. 179-185, XP009022566.
Koletzko, B., et al., Growth, development and differentiation: a functional food science approach, British Journal of Nutrition, vol. 80, Suppl. 1, 1998 pp. S5-S45, XP009027350.
Lo, C., "Infant formula, past and future: opportunities for improvement," American Journal of Clinical Nutrition, vol. 63, No. 4, 1996 pp. 646S-650S, XP-002102415.
"Growth, development and differentiation: a functional food science approach," article, written by Koletzko, et al., British Journal of Nutrition, 1998. (41 pages).
"Nutritional and biochemical properties of human milk: II. Lipids, micronutrients, and bioactive factors," abstract, Clin Perinatol., 1999. (1 page).
"Dietary modulation of the human gut microflora using prebiotics," abstract, Br J Nutr., 1998. (1 page).
"Dietary modulation of the human gut microflora using prebiotics oligofructose and inulin," abstract, J Nutr., 1999. (1 page).
"Prebiotic effects of inulin and oligofructose," abstract, Br J Nutr., 2002. (1 page).
"Fructooligosaccharides and *Lactobacillus acidophilus* modify gut microbial populations, total tract nutrient digestibilities and fecal protein catabolite concentrations in healthy adult dogs," abstract, J Nut., 2002. (1 page).

* cited by examiner

*Primary Examiner* — Brian J Gangle
(74) *Attorney, Agent, or Firm* — K&L Gates LLP

(57) ABSTRACT

The present invention pertains to a composition for inducing a pattern of gut barrier maturation similar to that observed with breast-feeding and able to improve gut barrier maturation, e.g. during neonatal stress. In particular, the present invention relates to an infant formula containing a combination of specific ingredients designed to provide a synergistic effect all along gastrointestinal tract and barrier function.

5 Claims, 1 Drawing Sheet

NUTRITIONAL FORMULA FOR OPTIMAL GUT BARRIER FUNCTION

This application is the National Stage of PCT/EP04/06736, filed Jun. 22, 2004, which claims priority to EPO 03014040.4, filed on Jun. 23, 2003.

BACKGROUND

The present invention pertains to a composition for inducing a pattern of gut barrier maturation similar to that observed with breast feeding and able to improve gut barrier maturation, e.g. during neonatal stress. In particular, the present invention relates to an infant formula containing a combination of specific ingredients designed to provide a synergistic effect all along gastrointestinal tract and barrier function.

During the postnatal development, the newborn intestine experiences a process of maturation that ends by the establishment of a functional barrier to macromolecules and pathogenic bacteria. This phenomenon is called gut closure and appears to be affected by the diet. Hence, different studies with infants (JPGN, 1995, 21: 383-6) and animal models (Pediatr Res, 1990, 28: 31-7) show that the maturation of the barrier is faster in breast-fed than in formula-fed newborns. This could explain the higher prevalence of allergy and infection in infants fed formula than in those fed with mother milk.

An impressive number of different mechanisms integrate this barrier, mechanisms that act synergistically to protect the host from the luminal aggressions. The first barrier consists on the intestinal epithelium, a continuous monolayer of columnar epithelial cells sealed together by protein complexes, such as the tight junctions. The second is a non-specific barrier composed by mechanisms that protect the mucosal surface as saliva, gastric acidity, mucus layer, proteolytic digestion, alkaline intestinal pH, unstirred layer and intestinal peristalsis. The gut immune system (GALT) is able to respond selectively and specifically to the foreign molecules and pathogen microorganisms. Finally, and not less important, intestinal flora directly and indirectly protect against host invasion by pathogens and macromolecules with antigenic properties.

Moreover, physical stress due for instance to antibiotherapy, disease or surgery and psychological stress induced for instance by hospitalization or prolonged separation from the mother, common situations in the preterm infant population, may impair further the maturation of the intestinal barrier and delay closure. Therefore, microbial flora has shown to affect the status of various mechanisms of the intestinal barrier (mucus layer, tight junctions) and both physical and psychological stress has been related to increased permeability to macromolecules, small solutes and bacteria.

In the art several means have been proposed to improve gut barrier function or gastrointestinal health in infants. For example, in U.S. Pat. No. 6,132,710, purified *Lactobacillus salivarius* and *Lactobacillus plantarum* strains are administered to preterm infants to prevent injury caused by infection and inflammation to mucosal tissue, especially by nasogastric administration to prevent gastrointestinal tissue injury in neonatal necrotizing enterocolitis.

Also, JP 5030942 provides a food and drink containing active component of milk fat globule membrane (MFGM), which can control permeability of high molecular substances, such as protein, through intestine vessel. It is useful for prevention and therapy of food allergic disease.

As regards to gut barrier immunity, WO 9700078 provides a protein hydrolysate for down-regulating hypersensitivity reactions and for promoting the gut immune barrier, which is made by hydrolyzing proteins with: (a) enzymes derived from a preparation containing probiotic gastrointestinal bacteria and (ii) a protease system similar to that of Lactobacillus GG and (b) pepsin and/or trypsin.

Though those microorganisms or ingredients bring about a great potential of beneficial effects for the individual incorporating them, a disadvantage resides in that said microorganisms or ingredients only exert their effect in limited parts of the intestine and on individual mechanisms of the intestinal barrier.

Therefore, an object of the present invention resides in obviating the disadvantages of the prior art and providing improved means to promote simultaneous maturation of various mechanisms of the gut barrier and this all along the intestine during formula feeding, in order to induce a pattern of gut barrier maturation similar to that observed with breast-feeding.

SUMMARY

During the studies leading to the present invention the present inventors observed an unexpected effect implying that the above object may be solved by providing specific combinations of bioactive ingredients that can be associated to a microorganisms able to deliver at least one of said ingredients all along the intestine.

These specific combinations of ingredients comprise at least one substance selected from the group consisting of specific fats (gangliosides, LC-PUFAs) or non-digestible carbohydrates, such as oligosaccharides, for example.

The specific microorganisms according to the present invention that may be used as part of the combinations for delivering said substances able to improve the gut barrier maturation to specific parts of the gastrointestinal tract thereof. The microorganisms differing in their ability to survive in the different parts of the gastro-intestinal tract can be incorporated in a cocktail. Some of said substances can be added to the microorganism cocktail in order to reinforce their effects by stimulating the maturation of barrier mechanisms different to those stimulated by the microorganisms.

These combinations of ingredients could be included in pre-term and starter infant formulas that, by improving barrier maturation could also reduce the risk of allergy and infection.

Thus, according to the present invention, a nutritional formula designed for improving gut barrier maturation and an optimal barrier function in infants, comprises one of the above combinations of ingredients, associated with at least one microorganism, supplemented in an amount efficient to induce a pattern of gut barrier maturation similar to that observed with breast-feeding.

A further object of the present invention relates to the use of such specific ingredient combinations to improve gut barrier maturation and barrier function in infants, thus reducing the risk of developing allergy and infection.

In another embodiment, the present invention relates to the use of the said ingredients to improve the gut barrier homeostasis during the suckling period in healthy infants and in those suffering from physical or psychological stress.

In a last aspect, the invention provides a method for improving gut barrier maturation and an optimal barrier function in infants, comprising the step of administering to the individual a combination of at least one ingredient selected from the group consisting of specific fats or non digestible oligosaccharides said ingredients being associated with at least one microorganism.

Additional features and advantages are described herein, and will be apparent from, the following Detailed Description and the figures.

DETAILED DESCRIPTION

Figure 1:
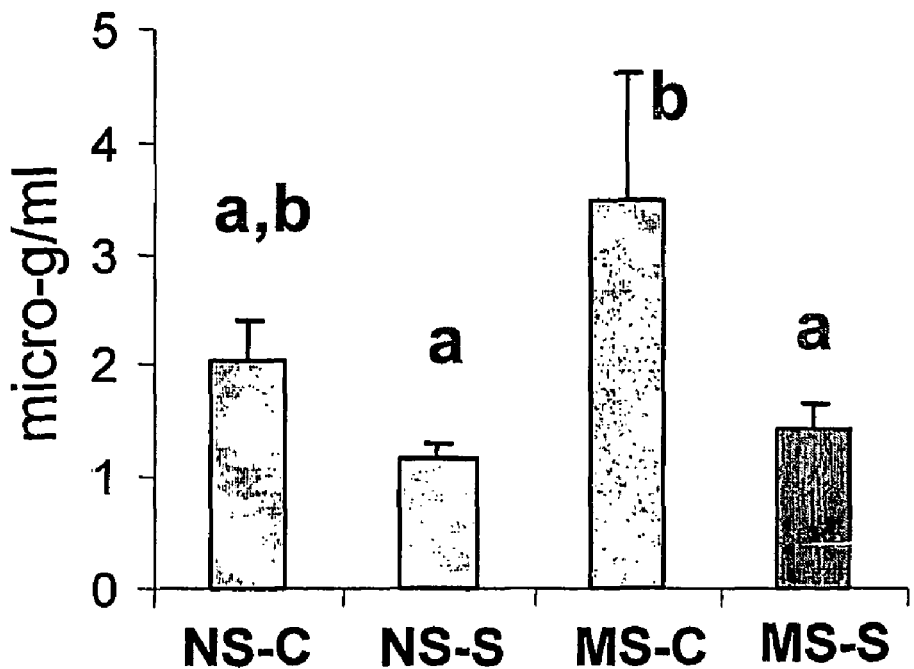
FIG. 1 represents plasma concentration of FITC-dextran (A) and HRP (B) in handled (NS-) or maternally deprived rats (MS) at PND 36 fed with either control (-C) or supplemented (-S) diets. Plasma was collected 150 min after administration of the permeability probe solution by intragastric gavage. Mean±SEM of 8 animals is shown. Different letters indicate significant differences ($p<0.05$).
Figure 1:
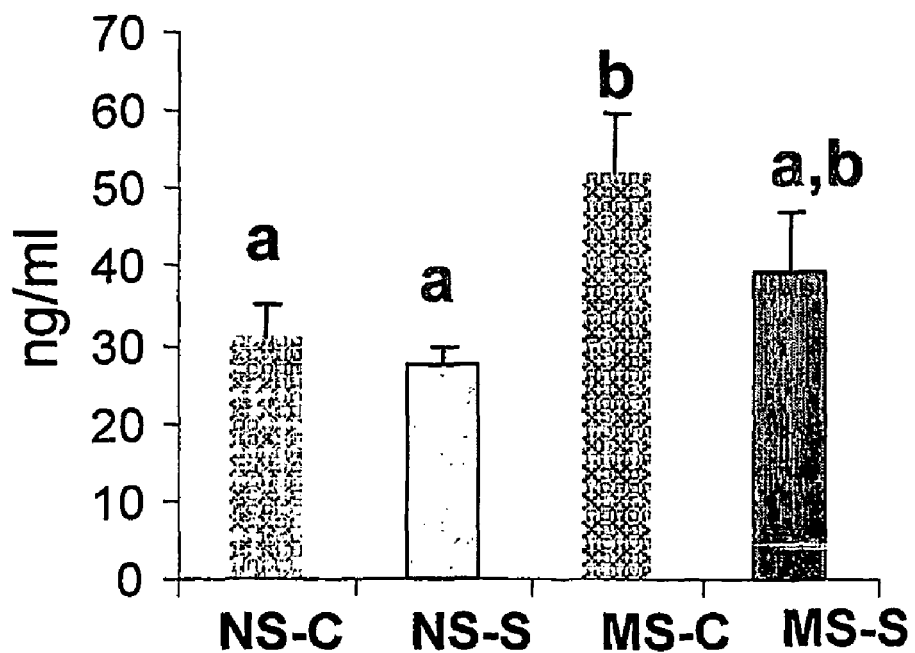

In the following description, the term "Low birth weight (LBW) formula" means formula specifically designed for feeding the LBW infant. The LBW infant is defined as an infant weighing less than 2500 g at birth. This infant may be either a "premature" infant (i.e. born before the $37^{th}$ week of gestation) or a "small-for-date" infant (i.e. an infant born between the $37^{th}$ and 41st week of gestation but showing a retarded intra-uterine growth). The LBW formula can be used as soon as enteral feeding is possible and until the LBW infant achieves a body weight similar to the birth weight of full-term infant (2500 g-4000 g) or for the further weeks until 5000 g.

The term "Starter formula" means formula specifically designed for feeding infants during the first 4-6 months of life and fulfilling the totality of their nutritional requirements.

According to a first aspect, the following substances may be part of the combination which can improve barrier maturation all along the intestine during formula feeding:

Non-digestible carbohydrates, such as fructo-oligosaccharides (FOS), galacto-oligosaccharides (GOS), inulin, Arabic gum, xylo-oligosaccharides, resistant starch and the like and LC-PUFA, such as arachidonic acid (AA) or docosahexanoic acid (DHA)

and optionally

Human milk oligosaccharides, such as sialyllactose and/or

Gangliosides such as those contained in delactosed whey from buffalo milk, and/or Milk or colostrum fractions, such as acid, rennet or micellar casein, acid, sweet or ultra whey, fat globules membranes and the like, and/or Extensive hydrolysed protein, such as those obtained from whey protein hydrolysis, and/or Polyamines such as spermine or spermidine and/or one or more polyamine precursors, in particular ornithin and arginine Preferably, non-digestible carbohydrates may be selected in the group of fructo-oligosaccharides, galacto-oligosaccharides, sialo-oligosaccharides, xylo-oligosaccharides, inulin, arabic gum, guar gum, resistant starch and/or milk-derived oligosaccharides and be added to the microorganism cocktail. One or more of these can be used in the total doses of from about 0.01 to 5 g/100 ml, and preferably 1-2 g/100 ml. A mixture of two or more carbohydrates may be used, each carbohydrate ranging between the 5% to 95% of the carbohydrate mixture.

Preferably, particular lipids may be used. For instance, an effective amount of at least one n-6 polyunsaturated fatty acid in combination with at least one n-3 polyunsaturated fatty acid, such as C20 or C22 n-6 fatty acid and one C20 or C22 n-3 fatty acid. The C20 or C22, n-6 fatty acid is present in a total amount of about 0.01 to 6.0% by weight of all fatty acids in the composition, preferably in a total amount of 0.1 to 1%. The C20 or C22 n-3 fatty acid is included in a total amount of about 0.01 to about 6.0% by weight of all fatty acids in the composition, preferably in a total amount of 0.1 to 1%. Preferably, the n-6 polyunsaturated fatty acid used in the present invention is arachidonic acid (AA, C20:4 n-6) and the n-3 polyunsaturated fatty acid used in the present invention is docosahexanoic acid (DHA, C22:6, n-3). The effective AA: DHA ratio is about 1:1 to 2.5:1, and preferably 1:1 to 2:1. The source of the LC-PUFA may be egg lipids, fungal oil, low EPA fish oil, algal oil, etc.

Gangliosides, a second class of lipids, may also be added to the combination of ingredients, for example in an amount of from about 1-20 microMol/L formula, and preferably 6-15 microMol/L. The source of gangliosides may be cow's milk, cow's colostrum, but preferably buffalo's milk, milk serum or colostrum, goat's milk, colostrum or serum and/or derivatives of either.

The combination may also contain polyamines, in particular spermidine, spermine, or putrescine and/or one or more polyamine precursors, in particular ornithin and arginine. They can be used in an amount of about 10 to 2,000 microg/100 g solid formula. The polyamine is preferably at least two or more selected from the group consisting of spermine, spermidine, putrescine and cadaverine. Preferably the composition comprises about 10-90% of spermine, 10-90% of spermidine, 0-90% of putrescine and 0-20% of cadaverine.

Preferably, the milk fractions (enriched in growth factors) may be in the form of fat globule membrane proteins, acid, rennet or micellar casein, acid, sweet or ultra whey, whey protein hydrolysates, for example. They can be used in an amount of about 0.01 to 7 g/100 ml formula, and preferably 0.5-3 g/100 ml.

According to another aspect, any or several of the former substances may be associated with microorganisms, as delivering agents.

The microorganisms to be used contain at least one substance the release thereof at the specific location will result in a beneficial effect on the barrier maturation. The microorganisms to be used can be specifically designed, treated or modified to ensure the release at the specific location.

Examples for a specific delivery to the small intestine are e.g. substances that interact locally with the mucus layer of the host, aggregate pathogens and facilitate their elimination by mucus flushing substances, e.g. substances that complex macromolecules and reduce their ability to permeate, e.g. enzymes that have the property to digest pathogen virulence factors (such as enterotoxins). Examples for a delivery to the colon are e.g. substances that have detoxifying properties, substances that have the potential to control the motility pattern of specific gut portions, substances that have the potential to favor intestinal cell differentiation, such as polyamines, substances that have the potential to increase innate immunity or substances that have the potential to restore the mucus layer integrity.

In order to provide a microorganism containing one or more substances of interest any microorganism may be selected, that inherently expresses such substances. Since the microorganisms are designed to release their intracellular material including the beneficial substance(s) at a specific location of the gut, a secretion of the substance into the environment is not required. On the contrary, according to the present invention the substance will be present in higher amounts at the predetermined location, since essentially all of the microorganism utilized will lyse and release the substance there. To this end, the corresponding microorganisms already containing the respective substance may optionally be pretreated in a manner appropriate to deliver the substance up to a certain desired location of the gut and may be administered to a recipient, whereupon they will lyse at the respective location in the gut depending on the sort of pretreatment.

This is a great advantage as compared to the common use of probiotics, wherein beneficial substances are primarily released by means of secretion into the environment. According to the present invention the microorganism utilized will release all of its beneficial cargo essentially at the same time when arriving at the location of the gut, where it is designed to lyse. In addition, the amount of the corresponding substance to be delivered to a recipient may also be more properly controlled, since a given amount of the microorganism to be used will be administered, with the content of the substance of interest being by and large known.

In order to increase the amount of the said substances to be delivered by the microorganism common techniques may be used, such as applying particular fermentative conditions or genetically modifying the microorganism itself, by e.g. subjecting the microorganisms to a random mutagenesis and selecting those mutants expressing a higher amount of the desired substance. Yet, also recombinant means may be applied, wherein the expression of the endogenous gene is increased by e.g. linking the corresponding gene with a promotor stronger than the endogenous one, or by inserting the gene or genes encoding the substance(s) of interest into the microorganism on a plasmid or into the chromosome thereof, optionally linked with a strong promoter that drives the expression of the gene(s) of interest such that the recombinant microorganism will contain higher amounts of the desired substance.

Depending on the nature and duration of the pretreatment the endurance of the microorganism, i.e. its survival in the gastrointestinal tract may be established, with potential locations of delivery being the stomach, the duodenum, the jejunum, the ileum or the colon. The microorganisms to be added in the present formula may be selected from the group consisting of *Lactobacilli, Bifidobacteria, Streptococci, Pediococci, Enterococci, Lactococci, Oenococci, Staphylococci, Bacteroides*, Yeasts or mixtures thereof. Preferred examples of such microorganisms are Bad 4, B128, B129, *Lactobacillus jonhsonii* or *Lactobacillus paracasei* ST11, all of which are freely available from Depository Institutes under the accession numbers CNCM I-2168, CNCM I-2169, CNCM I-2170, CNCM I-1225 and CNCM I-2116, respectively. Also, *Streptococcus thermophilus* (TH4) or *Bifidobacterium lactis* (Bb12 (ATCC27536)) may be used. They are provided by Hansen (Chr. Hansen A/S, 10-12 Boege Alle, P.O. Box 407, DK-2970 Hoersholm, Danemark). Also *Bifidobacterium longum* BB536 (provided by Morinaga) may be used.

Once a microorganism has been selected and optionally pretreated, said microorganism may be included in a LBW, starter or follow-up formula, or in a baby food as a powder obtained by freeze- or spray-drying, for example in an amount of from $10^5$-$10^{13}$ cfu/100 g, depending on the nature of the substance to be delivered and the amount of the substance contained in the respective microorganisms.

The above ingredients are conveniently administered in form of a product acceptable to the consumer, such as an ingestable carrier or support, respectively. Examples for such carriers or supports are a pharmaceutical or a food or petfood composition. Non-limiting examples for such compositions are milk, yogurt, curd, cheese, fermented milks, milk based fermented products, fermented cereal based products, milk based powders, infant formula, liquid bacterial suspensions, dried oral supplement, wet oral supplement, dry tube feeding or wet tube feeding.

The nutritional compositions are preferably in the form of a complete diet such that, when used as the sole source of nutrition, essentially covers all daily energy, nitrogen, lipid, vitamin, mineral and trace elements. However, the nutritional composition may also be in the form of a supplement.

In a preferred embodiment, the present invention provides an infant formula, which may be in the form of a low birth weight or a starter infant formula, for example. It may comprise apart the combination of specific ingredients as mentioned above, a protein source, a carbohydrate source, and a source of lipids.

The source of protein may be any suitable dietary protein; for example animal proteins (such as milk proteins, meat proteins and egg proteins), vegetable proteins (such as soy, wheat, rice or pea proteins), mixtures of free amino acids, or combination thereof. Milk proteins such as casein, whey proteins and soy proteins are particularly preferred. In a preferred embodiment, the protein source comprises about 1.8 to about 4 grams per 100 kcal of formula.

If the formula includes a fat source, the fat source preferably provides about 5% to about 55% of the energy of the nutritional formula; or about 3 to 7 grams per 100 kcal of formula; The lipids making up the fat source may be any suitable fat or fat mixture. Vegetable fats are particularly suitable; for example soy oil, palm oil, coconut oil, safflower oil, sunflower oil, corn oil, canola oil, lecithins, and the like. Animal fats such as milk fats may also be added if desired.

If the formula includes a carbohydrate source, the carbohydrate source preferably provides about 40% to about 80% of the energy of the nutritional formula or about 6 grams to about 15 grams per 100 kcal of formula, for example. Any suitable carbohydrates may be used, for example sucrose, lactose, glucose, fructose, corn syrup solids, and maltodextrins, and mixtures thereof.

Suitable vitamins and minerals may be included in the nutritional formula in the usual manner to meet the appropriate guidelines. One or more food grade emulsifiers may be incorporated into the nutritional formula if desired; for example diacetyl-tartaric acid esters of mono-diglycerides, lecithin and mono- and di-glycerides. Similarly suitable salts and stabilisers may be included.

This formula is preferably enterally administrable; for example in the form of a powder, a liquid concentrate, or a ready-to-drink beverage. It may be prepared in any suitable manner, for example, by blending together the source of dietary protein, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water that has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenized; for example in two stages.

The liquid mixture may then be thermally treated to reduce bacterial loads. For example, the liquid mixture may be rapidly heated to a temperature in the range of about 80° C. to about 150° C. for about 5 seconds to about 5 minutes. This may be carried out by steam injection, autoclave or by heat exchanger; for example a plate heat exchanger. The liquid mixture may then be cooled to about 60° C. to about 85° C.; for example by flash cooling. The liquid mixture may then be again homogenized; for example in two stages at about 7 MPa to about 40 MPa in the first stage and about 2 MPa to about 14

MPa in the second stage. The homogenized mixture may then be further cooled to add any heat sensitive components; such as vitamins and minerals. The pH and solids content of the homogenized mixture is conveniently standardized at this point.

If it is desired to produce a powdered nutritional formula, the homogenized mixture is transferred to a suitable drying apparatus such as a spray drier or freeze drier and converted to powder. The powder should have a moisture content of less than about 5% by weight.

If it is desired to produce a liquid formula, the homogenized mixture is preferably aseptically filled into suitable containers. Aseptic filling of the containers may be carried out by pre-heating the homogenized mixture (for example to about 75 to 85° C.) and then injecting steam into the homogenized mixture to raise the temperature to about 140 to 160° C.; for example at about 150° C. The homogenized mixture may then be cooled, for example by flash cooling, to a temperature of about 75 to 85° C. The homogenized mixture may then be homogenized, further cooled to about room temperature and filled into containers. Suitable apparatus for carrying out aseptic filling of this nature is commercially available. The liquid formula may be in the form of a ready to feed formula having a solids content of about 10 to about 14% by weight or may be in the form of a concentrate; usually of solids content of about 20 to about 26% by weight. Flavors may be added to the liquid formulas so that the formulas are provided in the form of convenient, flavorsome, ready-to-drink beverages.

This composition may be particularly designed for healthy infants, infants suffering from gut microflora alterations, such as after antibiotic treatment and, infants suffering from physical and psychological stress resulting, for example, from disease, surgery, hospitalization, prolonged separation from the mother, in order to improve gut barrier maturation and thus reduce the risk of allergy and infection. The amount of the formula required to be fed to the infant will vary depending upon factors such as the infant's condition, the infant's body weight, the age of the infant, and whether the formula is the sole source of nutrition. In general, sufficient of the nutritional composition is administered to provide the infant with about 1 g protein to about 4.0 g protein per kg of body weight per day supplemented with the ingredients according to the present invention in the amounts as indicated above. If the nutritional composition is used as a supplement to other foods, the amount of the nutritional composition that is administered daily may be decreased accordingly.

Example 1

Effects of LC-PUFA, *Lactobacillus paracasei* CNCM I-2116 and FOS/GOS on Intestinal Permeability The specific effects of neonatal stress on the intestinal barrier are starting to be documented. Different studies in rats showed that intermittent maternal deprivation during the neonatal period results in higher intestinal permeability at weaning and later in life. With this study, we intended to assess the effect of feeding a diet supplemented with a blend of LC-PUFA, probiotic bacteria and non-digestible oligosaccharides on intestinal permeability of young rats that suffered a maternal deprivation protocol during the neonatal period.

Methods:
Animals
Primiparous time-pregnant female Long-Evans Hooded rats were purchased from Janvier (France), arriving to our animal care facility on gestational day 12. They were individually housed till delivery under constant temperature and humidity, and maintained on a 12:12 dark:light cycle. Food and water were provided ad libitum. Housing conditions were kept for all the duration of the protocol.

One day after delivery (postnatal day 2—PND2), dams were removed from their maternity cages and the sex of the pups was determined. Standardized litters of 8 male pups were randomly assigned for fostering.

Neonatal Stress

The dams and their pups were assigned to one of two rearing conditions: 1) maternal separation groups, exposed to a 180 min period of daily maternal separation on PND 2 to 14 (MS), or 2) handled controls, exposed to daily manipulation (weighing and 15 min handling) but not to maternal separation (NS).

At 9 am, the dams were removed from their home cage and kept in waiting cages throughout the 3 hrs separation period (MS dams) or 15 min handling period (NS dams). Each MS litter was removed from the nest, weighed, and placed as a group in an isolation cage in an adjacent room. The isolation cages were kept at 32.0±0.5° C. At the end of the separation period pups were returned to their home cage and rolled in the soiled bedding before reuniting them with their foster mother. Litters from the NS groups were treated similarly but instead the 3 hours separation period, they were gently handled for 15 min.

Fifty percent of the soiled bedding of the home cage was replaced with clean bedding once a week.

Experimental Protocol

Pups were definitely separated from their foster mothers at PND 15. At that time, the pups from each group were randomized by weight and distributed into 2 groups of MS and 2 groups of NS animals. The pups from each of those four groups were housed together (8 animals/cage) up to PND 21. Then, they were individually housed until the end of the study.

From PND 15 to PND 36, animals received either control (groups MS-C and NS-C) or supplemented (groups MS-S and NS-S) diet ad libitum. Diet was replaced by a fresh batch every morning.

At PND36, —after 30 min fasting and 150 min before the sacrifice—animals received 1 ml/100 g BW permeability probe solution by intra gastric gavage. The solution contained 100 mg/ml FITC-Dextran 70 KDa (Sigma FD-70S) and 20 mg/ml horseradish peroxidase (type II HRP, Sigma P8250)

At sacrifice, animals were anesthetized with isoflurane. Blood was sampled at the dorsal aorta. Plasma was obtained by centrifugation and used within hours for the analysis of the permeability probes Diets Animals were fed from PND15 till PND 36 with nutritionally adapted semisynthetic diets (modified AIN 93 G) whose composition is shown in table 1. Supplemented (S) diet contained the following functional ingredients: *Lactobacillus paracasei* CNCM I-2116 (so called ST11) ($\times 10^{10}$ ST11 100 g diet); 0.4 g/100 g diet fructo-oligosaccharides (FOS, Raftilin® HP, Orafti® SA, Belgium), 3.6 g/100 g diet galacto-oligosaccharides (GOS, Vivinal™ GOS 10, Borculo™ Domo Ingredients, The Netherlands), 2 g/100 g fatty acids Arachidonic acid (AA, ARASCO®, Martek, USA), and 2 g/100 g fatty acids docosahexaenoic acid (DHA, DHASCO®, Martek, USA). Control (C) diet contained fresh MRS—replacing ST11—, maltodextrin (Glucidex® D12, Roquette Freres, France) and lactose (Fluka®, 61340)—instead of the oligosaccharides—and increased proportion of cocoa butter and corn oil—replacing DHASCO® and ARASCO®.

Fresh batches of diets were prepared every week, distributed in daily doses, which were conditioned in aluminium bags under $N_2$ atmosphere and negative pressure and frozen at $-20°$ C. until use.

TABLE 1

Composition of the diets.

| | Control diet | Supplemented diet |
|---|---|---|
| | (per 100 g diet) | |
| K-caseinate (g) | 20.00 | 20.00 |
| Corn Starch (g) | 32.95 | 32.95 |
| Maltodextrin (g) | 20.74 | 12.58 |
| Sucrose (g) | 10.00 | 10.00 |
| Lactose (g) | 4.26 | — |
| Raftilin HP (g) | — | 0.42 |
| Vivinal GOS 10 (g) | — | 12.00 |
| Fat mix (g) (see below for composition) | 7.00 | 7.00 |
| Mineral mixture (AIN-93-G) (g) | 3.50 | 3.50 |
| Vitamine mixture (AIN-93-VX) (g) | 1.00 | 1.00 |
| L-Cysteine (g) | 0.30 | 0.30 |
| Cholinhydrogentartrate DAB 10 (g) | 0.25 | 0.25 |
| MRS (ml) | 0.80 | — |
| ST11 culture ($5 \times 10^{10}$ cfu/ml) (ml) | | 0.8 |
| Fat mix: | g/100 g fat mix | |
| Soybean oil | 25.12 | 26.44 |
| Trisun 80 | — | 2.59 |
| Cocoa butter | 30.26 | 27.12 |
| Corn oil | 44.63 | 34.22 |
| ARASCO | — | 4.70 |
| DHASCO | — | 4.93 |

Permeability probes were analysed in plasma of the animals. FITC-dextran concentration was assessed in a fluorimeter at $\lambda$ex 485 nm/$\lambda$em 535 nm. HRP was analysed using TNB substrate (Sigma T0440), and measuring OD of the reaction product at 340 nm.

Statistics

Data are expressed as mean±SEM. The normality and homoscedasticity of the data were checked in each group. Comparisons were done by two-way ANOVA (two factors: neonatal stress and diet) followed by a Fisher Least Significant Difference (LSD) to assess the differences between the groups.

Results

Results are shown in FIG. 1. As expected, the concentration of dextran and HRP was or tended to be higher in the animals having suffered the maternal deprivation protocol (MS-C vs NS-C). Conversely, MS animals fed with the supplemented diet showed dextran and HRP concentration that was or tended to be lower than that found in MS animals fed the control diet (MS-S vs MS-C) and not significantly different from the animals that did not suffered the neonatal stress.

We concluded that maternal separation increases in rats the intestinal permeability to proteins and other macromolecules and that a blend of functional ingredients containing LC-PUFA, oligosaccharides and one lactobacillus restores the intestinal permeability to normal levels.

Example 2

Formula for Low-Birth-Weight Infants

The formula has the following composition (per 100 g of powder): total fat 24 g, total protein 14.4 g, total carbohydrates 55.9 g, AA enriched oil (fungal) 0.87 g, DHA enriched oil (Low EPA fish oil) 0.44 g, FOS/inulin (70/30) 12 g, *S. thermophilus* Th4 (Chris Hansen) (freeze-dry powder, 10E12 cfu/g) 0.1 g, *B. lactis* ATCC 27536 (freeze-dry powder, 5×10E12 cfu/g) 0.15 g, Spermine/Spermidine mix (1/1) 0.1 mg, Sodium 180 mg, Potassium 530 mg, Chloride 280 mg, Phosphorus 320 mg, Calcium 490 mg, Magnesium 54 mg, Manganese 34 µg, Vitamin A 1500 IU, Vitamin D 490 IU, Vitamin E 9.8 IU, Vitamin C 79 mg, Vitamin K1 59 µg, Vitamin B1 0.29 mg, Vitamin B2 0.66 mg, Vitamin B6 0.37 mg, Niacin 4.9 mg, Folic acid 290 µg, Pantothenic acid 2.3 mg, Vitamin B12 1.1 µg, Biotin 11 µg, Choline 37 mg, Inositol 22 mg, Taurine 39 mg, Carnitine 7.9 mg, Iron 7.4 mg, Iodine 49 µg, Copper 0.44 mg and Zinc 3.7 mg.

The formula is reconstituted by mixing 142 g of powder to 900 mL of water to give 1 L of ready-to-drink preparation. The composition given above can vary to accommodate for local directives concerning the amounts of specific ingredients. Other trace elements (e.g. selenium, chromium, molybdenum, fluoride) may be added in adequate amount according to age.

Example 3

Starter Formula

A starter formula for infants (from birth to 4-5 months), in powder form is prepared. The formula has the following composition (per 100 g of powder): total fat 25.8 g, total protein 11.5 g, total carbohydrates 57.8 g, AA enriched oil (fungal) 1 g, DHA enriched oil (Low EPA fish oil) 1 g, FOS/inulin (70/30) 12 g, *L. paracasei* CNCM I-2116 (Spray-dry powder, 10E12 cfu/g) 0.1 g, *B. longun* BB536 (Morinaga) (Spray-dry powder, 5×10E12 cfu/g) 0.1 g, Sodium 120 mg, Potassium 460 mg, Chloride 360 mg, Phosphorus 160 mg, Calcium 320 mg, Magnesium 35 mg, Manganese 40 µg, Vitamin A 1500 IU, Vitamin D 310 IU, Vitamin E 6.1 IU, Vitamin C 41 mg, Vitamin K1 42 µg, Vitamin B1 0.31 mg, Vitamin B2 0.69 mg, Vitamin B6 0.38 mg, Niacin 3.8 mg, Folic acid 46 µg, Pantothenic acid 2.3 mg, Vitamin B12 1.1 µg, Biotin 11 µg, Choline 38 mg, Inositol 23 mg, Taurine 41 mg, Carnitine 8.2 mg, Iron 6.1 mg, Iodine 25 µg, Copper 0.31 mg and Zinc 3.8 mg.

The formula is reconstituted by mixing 132 g of powder to 900 mL of water to give 1 L of ready-to-drink preparation. The composition given above can vary to accommodate for local directives concerning the amounts of specific ingredients. Other trace elements (e.g. selenium, chromium, molybdenum, fluoride) may be added in adequate amount according to age.

Example 4

Starter Infant Formula

A starter formula for infants is prepared as in example 3, but replacing FOS/inulin by sialyl-lactose in an amount of 0.5 g. In this formula, half of the total protein will be furnished in the form of extensive whey protein hydrolyzate.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for improving gut barrier maturation in an infant, the method comprising:
   administering to the infant a nutritional composition comprising arachidonic acid, docosahexanoic acid, a non-digestible oligosaccharide comprising a milk-derived oligosaccharide, and at least one microorganism comprising *Lactobacillus paracasei CNCM* 1-2116, thereby improving gut barrier maturation.

2. The method of claim 1, wherein the nutritional composition is in a form of a complete diet, a supplement or a medicament.

3. The method of claim 1, wherein the nutritional composition is in a form of a low birth weight infant formula, a starter infant formula, a follow-up infant formula or a baby food.

4. The method of claim 1, wherein the nutritional composition is selected from the group consisting of milk, yogurt, curd, cheese, fermented milks, milk based fermented products, fermented cereal based products, milk based powders, infant formula, liquid bacterial suspensions, dried oral supplement, wet oral supplement, dry tube feeding, wet tube feeding and combinations thereof.

5. A method for improving gut barrier function in an infant, the method comprising:
   administering to the infant a nutritional composition comprising arachidonic acid and docosahexanoic acid, a non-digestible oligosaccharide comprising a milk-derived oligosaccharide, and at least one microorganism comprising *Lactobacillus paracasei CNCM* 1-2116, thereby improving gut barrier function.

* * * * *